United States Patent [19]

Knowles et al.

[11] 4,393,133

[45] Jul. 12, 1983

[54] HUMAN HEPATOMA DERIVED CELL LINE, PROCESS FOR PREPARATION THEREOF, AND USES THEREFOR

[75] Inventors: Barbara B. Knowles, West Chester; David P. Aden, Philadelphia, both of Pa.

[73] Assignee: The Wistar Institute of Anatomy and Biology, Philadelphia, Pa.

[21] Appl. No.: 158,685

[22] Filed: Jun. 12, 1980

[51] Int. Cl.³ .................. C12N 7/00; C12N 7/02; C12N 5/00; C12P 21/00; C12Q 1/68
[52] U.S. Cl. .................................. 435/6; 435/68; 435/240; 435/235; 435/239; 435/948; 436/63; 424/89; 436/820
[58] Field of Search ............. 435/240, 241, 4, 6, 435/948, 172, 68, 235, 239; 424/12, 86, 89

[56] References Cited

U.S. PATENT DOCUMENTS

| 3,871,954 | 3/1975 | Zuckerman | 435/235 |
| 4,164,566 | 8/1979 | Provost et al. | 424/89 |
| 4,209,587 | 6/1980 | Tolbert et al. | 435/240 |
| 4,237,224 | 12/1980 | Cohen et al. | 435/183 |

FOREIGN PATENT DOCUMENTS 2034323 6/1980 United Kingdom ............... 435/172

OTHER PUBLICATIONS

Aden et al., *Nature*, 282 615–616 (1979).
Reid, "Cloning", *Methods in Enzymology*, vol. LVIII, Academic Press, New York, 152, 153, 162–164 (1979).
Langenbach et al., *Chemical Abstracts*, 91:155286a, (1979).
Iwadare, *Chemical Abstracts*, 90:197313s, 7 (1979).
Martin et al., *Proc. Nat'l. Acad. Sci. USA*, 72 (4), 1441–1445 (1975).
MacNab et al., *Br. J. Cancer*, 34, 509–515 (1976).
Burrell et al., *Nature*, 279, 43–47 (1979).
Aleksanyan, *Chemical Abstracts*, 90:201941q, 446 (1979).
Alexander et al., *S. African J. Med. Sci.*, 41, 89–98 (1976).

*Primary Examiner*—Esther M. Kepplinger
*Attorney, Agent, or Firm*—Howson and Howson

[57] ABSTRACT

Human hepatoma cell lines, useful for metabolic studies such as screening potential carcinogens and mutagens, for cultivation of viruses, and for preparation of vaccines is obtained by culturing human hepatocarcinoma or hepatoblastoma on lethally irradiated cell feeder layers in the presence of a culture medium.

9 Claims, 2 Drawing Figures ng HBsAg-SUPERNATANT (■), CELL LYSATE (□)
μg ALBUMIN (▲) μg AFP (●)

HUMAN HEPATOMA DERIVED CELL LINE, PROCESS FOR PREPARATION THEREOF, AND USES THEREFOR

The invention described herein was made in the course of work under a grant or award from the Department of Health, Education and Welfare.

BACKGROUND OF THE INVENTION

There have been many attempts to develop cell culture systems for metabolic studies of chemicals, particularly for the short term assay of potential carcinogens and mutagens. The cell cultures in general use for such purposes are derived from rodents and, although they actively metabolize chemicals generally thought to be carcinogenic, the metabolites are different from those produced in normal human primary cultures. Human fibroblastic cell strains have been tested for their ability to convert potential carcinogens and mutagens to active carcinogens, but their ability to effect such metabolic conversions is low.

There are a number of problems associated with the growth of viruses for the production of vaccines. In particular, fastidious viruses, such as hepatitis B virus (HBV), have not been propagated successfully in cell cultures. Thus, cell culture systems capable of rapid growth which support production of viral components must be found in order for a vaccine to be produced from such fastidious viruses.

OBJECTS OF THE INVENTION

A primary object of this invention is to produce stable hepatic cell lines useful for drug metabolism studies and particularly for screening potential carcinogens and mutagens.

Another primary object of the invention is to produce hepatic cell lines useful in the production of hepatitis B viral components from which vaccines can be made.

A further object of this invention is a process for derivation of human hepatic cell lines useful in the screening of drugs and especially potential carcinogens and mutagens, for cultivation of viruses, and for preparation of vaccines.

Still another object of the invention is a method for producing a hepatitis B vaccine employing the hepatic cell lines of this invention.

These and other objects of this invention will become further apparent from the following specification, appended claims and accompanying drawings in which:

FIG. 1 is a plot of time in culture (days) vs. viable cell numbers $\times 10^{-6}$, and components of hepatitis B virus surface antigen (HBsAg), human albumin, and human α-fetoprotein (AFP) concentration in the cell active fluid, and FIG. II is an autoradiogram showing HBsAg in a control sample and in cell line Hep 3B of this invention, and the absence thereof in Hep G2 of said invention.

DETAILED DESCRIPTION OF THE INVENTION

Figure 1:
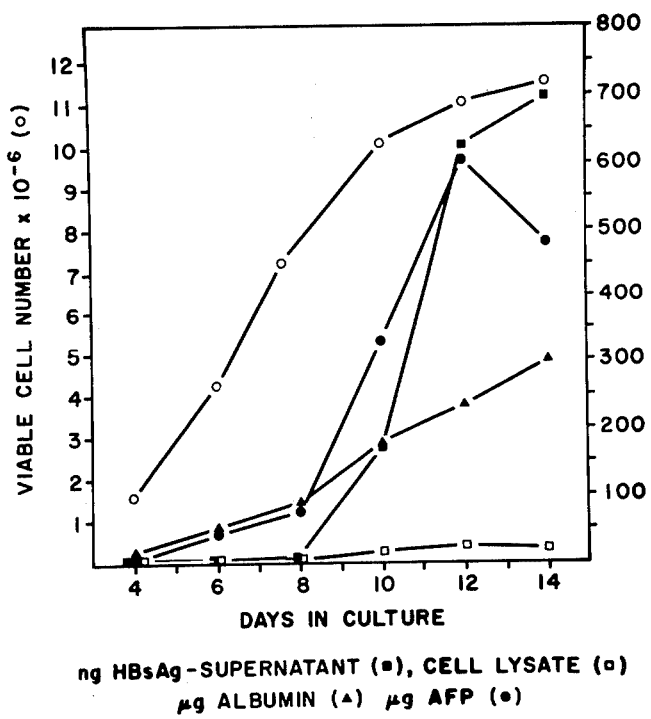
Figure 2:
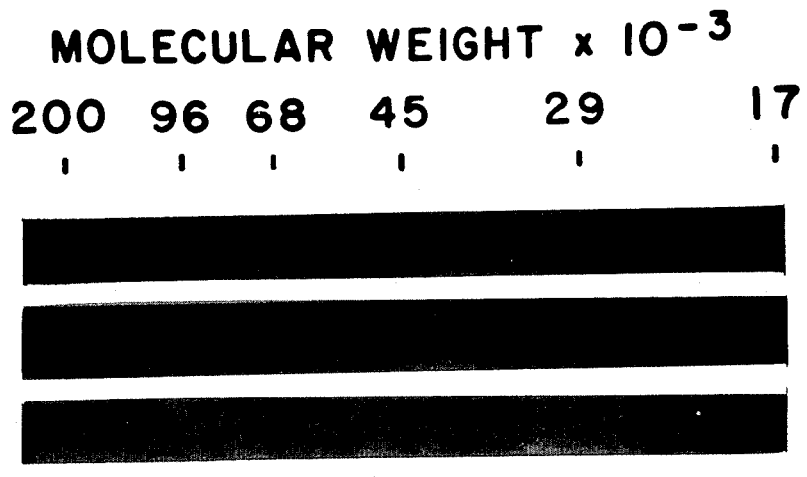

By the process of this invention there are produced novel stable cell lines suitable for use in metabolic studies, carcinogenesis and/or mutagenesis, and in the production of vaccines. The cell lines are obtained by culturing human hepatocarcinoma or hepatoblastoma on lethally irradiated cell feeder layers in the presence of a suitable culture medium. Although the present invention is applicable to the production of novel cell lines from any human hepatoma, it is described in greater detail hereinbelow in particular with the production of two specific cell lines designated Hep G2 and Hep 3B. These cell lines have been deposited with The Wistar Institute of Anatomy and Biology, 36th and Spruce Streets, Philadelphia, Pennsylvania 19104, and with the American Type Culture Collection (ATCC), Rockville, Maryland. Cell lines Hep G2 and Hep 3B have been assigned ATCC Nos. HB 8065 and HB 8064, respectively.

Cell lines designated Hep G2 and Hep 3B were derived as a result of biopsies taken during extended lobectomies of a 15 year old caucasian male from Argentina (1975) and an 8 year old black male from the United States (1976), respectively. The cells from which the cell line designated Hep 3B was derived, contained hepatitis B virus as can be seen by reference to FIGS. I and II, discussed below. However, this invention also contemplates infecting cells with HBV in order to produce HBsAg components for vaccine use.

Minces of the malignant tumors so obtained are cultured on lethally irradiated mouse cell layers designated STO in a cell culture medium consisting of Williams E medium (Gibco) supplemented with 10 percent fetal bovine serum (Reheis, Armour Pharmaceuticals). By the term "lethally irradiated" is meant that the cells have been irradiated to such a degree as to be incapable of replication. This procedure promotes the growth of differentiated cells with fastidious growth requirements while preventing overgrowth of contaminating fibroblastic cells.

The initial period of cell proliferation, may take place over a period of at least about three weeks, and if desired may continue for many weeks. Ordinarily an initial proliferation period of about four weeks is quite satisfactory, following which cell colonies are separated and transferred to new irradiated mouse cell (STO) feeder layers. Before transfer, cells from flasks containing single large colonies may be dissociated by trypsinization (0.25% trypsin, 0.1% ethylenediamine tetraacetic acid in Dulbecco's modified phosphate buffered saline solution lacking calcium and magnesium salts). The cell colonies are subsequently serially passaged at least about sixty times on STO feeder layers showing that they are established, routinely growing cell lines, each passage having a duration of about one week.

Sublines of both Hep G2 and Hep 3B which no longer require the presence of the STO feeder layer were selected (four years and two years after establishment of the biopsies in the case of Hep G2 and Hep 3B, respectively). Such sublines will proliferate if approximately $1 \times 10^6$ cells are placed in 12 ml. of cell culture medium, such as Eagle's minimal essential medium supplemented with 10 percent of fetal bovine serum in a flask containing approximately 75 cm.$^2$ of growth area for the cells after attachment to the substratum. Although the above-described culture medium is preferred, other culture medium formulations may be used for supporting growth of these cell lines.

These two specific cell lines, have been characterized as follows:

1. Chromosome number

Hep G2—the modal number of chromosomes is 55 (range 50–56). The cell line contains a marker chromosome which is a rearrangement of chromosome 1.

Hep 3B—the modal number is 60 with a subtetraploid mode of 82. This cell line contains a marker chromosome which is a rearrangement of human chromosome 1.

2. Human Plasma Proteins

The secreted products in the cell culture fluid of each cell line (Hep G2 and Hep 3B) have been characterized by both Ouchterlony double diffusion immuno precipitation analysis (using commercially available antibodies to human plasma proteins), and by two dimensional polyacrylamide gel electrophoresis, and are the following normal human plasma proteins:

TABLE I

| Human Protein | Cell Line | |
|---|---|---|
| | Hep G2 | Hep 3B |
| α-fetoprotein | + | + |
| albumin | + | + |
| α-2-macroglobulin | + | + |
| α-1-antitrypsin | + | + |
| α-1-antichymotrypsin | + | + |
| transferrin | + | + |
| haptoglobin | + | + |
| ceruloplasmin | + | + |
| plasminogen | + | + |
| $G_c$globulin | − | + |
| Complement (C'3) | + | + |
| Complement (C'4) | + | + |
| C'3 activator | + | − |
| α-1-acid glycoprotein | + | + |
| fibrinogen | + | + |
| α-2-HS glycoprotein | + | + |
| retinoic acid binding protein | + | + |
| β-Lipoprotein | + | + |

3. Production of HBsAg

Production of HBsAg has been quantitated in the Hep 3B cell line using the AUSRIA II (Abbott Labs.) solid phase radioassay (RIA) kit comparing positive values to a standard curve using purified HBsAg. See FIG. I in which the curve having points in the form of solid squares represents ng of HBsAg in cell culture supernatant vs. time, the curve having open square points represents ng HBsAg in cell lysate, and the curve having solid triangular points represents ug human albumin. The remaining curves having points in the form of solid and open ovals represent, respectively, ug of alpha-fetoprotein and viable cell number beginning with $10^6$ Hep 3B cells in 15 ml Eagle's minimal essential medium supplemented with 10 percent fetal bovine serum.

The components of HBsAg synthesized by Hep 3B were determined by pulse labeling the cells by exposure for 5 hours to 5 ml. Eagle's minimal essential medium free of fetal bovine serum, but containing 1 mCi of $^{35}$S-methionine (New England Nuclear Co.) and incubating 1.5 ml of $^{35}$S-methionine labeled cell supernatant with 10 microliters of guinea pig anti-HBsAg (obtained from National Institute of Allergy and Infectious Diseases, National Institute of Health, Bethesda, MD20014), and then with 20 λ rabbit antiserum to guinea pig immunoglobulin G. After an overnight incubation, immune complexes were obtained by centrifugation, washed and resuspended in a solution containing 1M dithiothreitol, 2% sodium dodecylsulfate and subjected to SDS polyacrylamide gel electrophoresis on a 7.5–15 percent linear gradient gel, dried, and exposed to Kodak NST2 film. The results obtained are illustrated in the autoradiogram of FIG. II, by reference to which it can be seen that p 23 and p 27 components of HBsAg are obtained from the sample of Hep 3B (see gel lane 2). These components are also present in the control sample containing purified HBsAg (gel lane 1), but are absent from Hep G2 which was not infected with HBV (gel lane 3).

The production of HBsAg components by cell line Hep 3B which contains the hepatitis B virus genome shows that these components can be purified for use in vaccine production or that by infecting hepatic cell lines produced by the process of this invention, similar components could be obtained for use in providing a HBV vaccine.

The following non-limiting examples are illustrative of various embodiments of this invention.

EXAMPLE I

This example illustrates the use of the cell line of this invention designated Hep G2 for metabolic studies, in particular for screening possible carcinogens and mutagens.

Confluent cultures of Hep G2 cells were exposed to 4.0 n moles ml. of $^3$H-benzo(a)pyrene (BP) in medium for 24 hours; most of the radioactivity was recovered in the medium. A significant portion of the BP was metabolized to water-soluble metabolites which, after treatment with β-glucuronidase yielded chloroform-extractable BP-quinones and 3-OH-PB. Of the chloroform-extractable material in the Hep G2 cell culture, the following metabolites were formed:

TABLE II

| Metabolite | Percent Metabolites Based on Total BP |
|---|---|
| BP 9,10 diol | 14 |
| BP 7,8 diol | 7 |
| Quinones | 6 |

Thus the Hep G2 cell line metabolizes BP to a number of oxidized derivations including the proximate carcinogenic metabolite BP-7,8 diol.

Studies of the BP-DNA adducts formed in the Hep G2 cells yielded the following results. Of 4.0 n moles of $^3$H-BP/ml of medium with 48 hour exposure, over 97 percent was metabolized. The DNA isolated from these cultures contained 28.2 p moles of bound BP/mg. DNA. The BP-DNA adducts resemble those formed in primary organ cultures from human tissue. Since it is generally accepted that polycyclic aromatic hydrocarbons, and many other classes of carcinogens, require metabolic activation to produce their biological effects and the Hep G2 cells metabolize these compounds to the activated form, the Hep G2 cells can be used as activators of carcinogens in a cell mediated mutation assay with other mammalian cells.

EXAMPLE II

Hep 3B was exposed to 0.5 n moles $^3$H-BP/ml. in medium for 24 hours, and 76 percent of the $^3$H-BP was metabolized to water-soluble intermediates. Of the chloroform-extracted material 76 percent was unchanged $^3$H-BP, but small amounts of the BP 9,10 diol and the BP 7,8 diol were detected.

As indicated previously the cell lines of this invention should be useful in the cultivation of viruses, particularly fastidious viruses such as HBV. In such use, monolayer cultures of the particular cell line, e.g. Hep G2, may be exposed either to Dane particles from infected patients' sera, or to HBV-DNA purified from such a source. After about an hour of absorption to the monolayer in small amounts of the culture medium, additional cell line culture medium may be added and the flasks containing the cell line incubated for several days. Monitoring of the cultures by standard techniques for detection of viral antigens, such as described above in connection with cell line Hep 3B, will determine the optimum time for harvest of cell cultures and virus antigen purification. The antigens so produced, e.g. HBsAg may be used for production of vaccines.

Where the initial hepatocarcinoma used in the process of this invention already contains the HBV genome, such as is the case with the source material from which the Hep 3B cell line was obtained, the HBsAg synthesized by the cell line can be used to produce a vaccine.

Advantageously, a cell line of this invention containing HBV, e.g. Hep 3B, provides an alternate source of HBsAg whereby the production and quality of the antigen may be controlled. Experiments with Hep 3B indicate that only a portion of the viral genome is present, and that infectious viral particles are not produced by this cell line, thereby eliminating the risk of HBV infection. Purification of the HBsAg from the cell culture medium for vaccine production can be effected by a number of well known methods in the art.

An alternative method of preparation of HBsAg from the cell lines of this invention involves the use of recombinant HBV-plasmid DNA in an in vitro HBsAg synthesizing bacterium. To prepare a vaccine employing this technique, the total cellular RNA, from which cDNA copies are made, or DNA from the HBsAg-producing cell line is isolated and digested with restriction enzymes that do not digest the HBV-DNA or leave the HBsAg coding segment in tact (e.g. Hind III), followed by enrichment of the HBV-DNA, either by hybridization to filters containing fixed Dane particle DNA and elution from the filters or by elution from electrophorograms after localization to a portion of the gel with radioactively-labeled Dane particle derived DNA. After reaction with dCMP residues, using nucleotidyl-terminal transferase, the DNA can be hybridized to plasmid pBR322, cleaved with PST-1 and tailed with d GMP residues, and E.coli can be transformed with hybrid plasmids and screened for HBsAg-producing colonies by methods well known in the art. HBsAg positive clones can then be selected, propagated and vaccine production from these clones would proceed (Wu, R. editor. Methods in Enzymology Vol. 68, Academic Press, N. Y. for overall recombinant DNA procedure).

We claim:
1. A process for assessing the metabolic conversion of chemicals and drugs considered to be potential carcinogens and mutagens, which comprises:
   (a) maintaining a culture of a human hepatic cell line selected from the group consisting of the cell lines designated Hep 3B and Hep G2 in a nutrient medium,
   (b) exposing said cell line to the chemical or drug to be tested,
   (c) analyzing said culture for the presence of metabolites of said chemical or drug, and
   (d) introducing said metabolites to cultures of other mammalian cells to determine their mutagenic capabilities.

2. The process according to claim 1 in which said cell line comprises Hep G2.

3. The process according to claim 1 in which said cell line comprises Hep 3B.

4. A process for isolation of hepatitis B virus surface antigen for use as a vaccine which comprises:
   (a) maintaining a human hepatic cell line, designated Hep 3B, which contains the hepatitis B virus genome in nutrient culture medium,
   (b) recovering the supernatant fluid from said culture, and
   (c) purifying the hepatitis B virus surface antigen in said supernatant fluid for use as a vaccine.

5. A process for isolation of human plasma proteins which comprises:
   (a) maintaining a human hepatic cell line which synthesizes plasma proteins selected from the group consisting of the cell lines designated Hep 3B and Hep G2 in a nutrient culture medium,
   (b) recovering the supernatant fluid from said culture, and
   (c) separating plasma proteins from said supernatant fluid, and purifying said plasma proteins.

6. The process according to claim 5 in which said cell line comprises Hep G2.

7. The process according to claim 5 in which said cell line comprises Hep 3B.

8. The cell line having the identifying characteristics of Hep 3B.

9. The cell line having the identifying characteristics of Hep G2.

* * * * *